(12) United States Patent
Casseday et al.

(10) Patent No.: US 7,915,307 B2
(45) Date of Patent: Mar. 29, 2011

(54) METHODS OF IMPROVING THE PHARMACOKINETICS OF DOXEPIN

(75) Inventors: Cara Baron Casseday, San Diego, CA (US); Elizabeth Ludington, San Diego, CA (US); Michael Skinner, San Diego, CA (US); Susan Dubé, Carlsbad, CA (US); Roberta L. Rogowski, Rancho Santa Fe, CA (US); Philip Jochelson, San Diego, CA (US); Robert Mansbach, San Diego, CA (US)

(73) Assignee: Somaxon Pharmaceuticals, Inc., San Diego, CA (US)

( * ) Notice: Subject to any disclaimer, the term of this patent is extended or adjusted under 35 U.S.C. 154(b) by 35 days.

(21) Appl. No.: 11/781,165

(22) Filed: Jul. 20, 2007

(65) Prior Publication Data
US 2008/0058407 A1 Mar. 6, 2008

Related U.S. Application Data

(60) Provisional application No. 60/833,617, filed on Jul. 24, 2006, provisional application No. 60/832,727, filed on Jul. 20, 2006.

(51) Int. Cl.
*A61K 31/335* (2006.01)
*A61P 25/22* (2006.01)
*A61P 25/24* (2006.01)
*A61P 43/00* (2006.01)

(52) U.S. Cl. ........................ 514/450; 514/923
(58) Field of Classification Search .................. 514/450, 514/923
See application file for complete search history.

(56) References Cited

U.S. PATENT DOCUMENTS

| | | | |
|---|---|---|---|
| 3,420,851 A | 1/1969 | Bloom et al. | |
| 3,438,981 A | 4/1969 | Stach | |
| 3,509,175 A | 4/1970 | Tretter | |
| 4,110,438 A | 8/1978 | Gahwyler | |
| 4,434,171 A | 2/1984 | Muller | |
| 5,030,632 A | 7/1991 | Sterling | |
| 5,116,852 A | 5/1992 | Gammans | |
| 5,332,661 A | 7/1994 | Adamczyk et al. | |
| 5,502,047 A | 3/1996 | Kavey | |
| 5,502,047 A | 3/1996 | Kavey | |
| 5,643,897 A | 7/1997 | Kavey | |
| 6,211,229 B1 | 4/2001 | Kavey | |
| 6,219,674 B1 | 4/2001 | Classen | |
| 6,344,487 B1 | 2/2002 | Kavey | |
| 6,407,128 B1 | 6/2002 | Scaife et al. | |
| 6,584,472 B2 | 6/2003 | Classen | |
| 6,683,102 B2 | 1/2004 | Scaife et al. | |
| 7,135,196 B2 | 11/2006 | Stockham | |
| 7,276,536 B2 | 10/2007 | Urata et al. | |
| 7,452,872 B2 | 11/2008 | Johnson | |
| 2002/0037828 A1 | 3/2002 | Wilson et al. | |
| 2002/0197235 A1* | 12/2002 | Moran | 424/85.5 |
| 2003/0235617 A1 | 12/2003 | Martino et al. | |
| 2005/0123609 A1 | 6/2005 | Hirsh et al. | |
| 2005/0239838 A1 | 10/2005 | Edgar et al. | |

FOREIGN PATENT DOCUMENTS
WO WO 99/40898 8/1999

OTHER PUBLICATIONS http://apma-nc.com/PatientEducation/INSOMNIA.HTM, 2000, 1-4.*
Prescription Drugs, http://www.grandtimes.com/Answer_Drugs.html, 1999, 1-3.*
Adapin, http://www.depression-guide.com/adapin.htm, 2005, 1-3.*
Somaxon's SILENOR™ Demonstrates Positive Results in Long-Term Phase 3 Clinical Trial in Elderly Patients with Insomnia, Somaxon Pharmaceuticals, p. 1-7, (Dec. 18, 2006).
Somaxon Pharmaceuticals Announces Positive Results in a Phase II Dose-Finding Study of Low-dose Doxepin in Adults with Primary Sleep Maintenance Insomnia, Somaxon Pharmaceuticals, p. 1-2, (Jan. 6, 2005).
Somaxon Pharmaceuticals Announces Positive Results in a Phase II Dose-Finding Study of Low-Dose Doxepin in Elderly Patients with Primary Sleep Maintenance Insomnia, Somaxon Pharmaceuticals, p. 1-3, (Apr. 21, 2005).
Somaxon Pharmaceuticals Announces Positive Phase 3 Results with SILENOR™ for the Treatment of Adults with Chronic Insomnia, Somaxon Pharmaceuticals, p. 1-5, (Apr. 10, 2006).
Somaxon Pharmaceuticals' SILENOR™ Demonstrates Positive Results in a Phase 3 Transient Insomnia Clinical Trial, Somaxon Pharmaceuticals, p. 1-5, (Oct. 23, 2006).
Somaxon Pharmaceuticals' SILENOR™ Demonstrates Positive Results in its Third Phase 3 Clinical Trial in Insomnia, Somaxon Pharmaceuticals, p. 1-6, (Nov. 20, 2006).
Shu et al., *Drug Metabolism & Disposition*, 18: 735-741, (1990).
Luo et al., *Drug Metabolism & Disposition*, 19:722-724, (1991).
Hobbs, *Biochem. Pharmacol.*, 18: 1941-1954, (1969).
Moody et al., *Drug Metabolism & Disposition*, 27: 1157-1164, (1999).
Denchle et al., *Psychopharmacology*, 131: 19-22, (1997).
Shu et al., *Drug Metabolism & Disposition*, 18: 1096-1099 (1990).
Grundstrom et al., *Sedative Properties of Doxepin in Comparison with Diazepam*, Psychopharmacology, 54: 165-169 (1977).
Richelson, *Tricyclic Antidepressants and Histamine H1 Receptors*, Mayo Clin Proc., 54:669-674, (1979).
Physicians Desk Reference, Litton Industries, p. 1211, 93, (1976).
Vincent et al., *Use of Human Sleep as a Test of Drug's Psychotropic Action with Doxepin as an example*, Bordeaux Medical, No. 10, 2650-51, 2653-54, 2657-57, and 2661, (1971).
Zung, *Effect of Antidepressant Drugs on Sleeping and Dreaming*, Excerpta Medica Foundation International Congress Series, No. 150, 1824-1826, (1968).
Ware, *Tricyclic Antidepressants in the Treatment of Insomnia*, Journal of Clinical Psychiatry, 44 [9, Section 2]: 25-28 (1983).
Technical Information/Summary of Drug Characteristics (SPC), Pfizer, p. 1-4, (2004).
*Physicians' Desk Reference*, p. 2434-2435, (1990).
*Physicians' Desk Reference*, p. 1849-1850, (1990).
*Physicians' Desk Reference*, p. 1310-1312, (1990).
Pecknold et al., *Trimipramine, Anxiety, Depression and Sleep*, Drugs, vol. 38: Suppl. 1, p. 25-31, (1989).

(Continued)

*Primary Examiner* — Sharmila Gollamudi Landau
*Assistant Examiner* — Kyle Purdy
(74) *Attorney, Agent, or Firm* — Knobbe, Martens, Olson & Bear, LLP

(57) ABSTRACT

Methods of improving the pharmacokinetics of doxepin in a patient.

24 Claims, 1 Drawing Sheet

OTHER PUBLICATIONS

Patent Information Leaflet, Sinequan™ (doxepin), United Kingdom, p. 1-2 (2002).
Nierenberg et al., *Management of Monoamine Oxidase Inhibitor-Associated Insomnia with Trazodone*, Journal of Clinical Psychopharmacol, vol. 9 No. 1, p. 42-45, (1989).
Nicholson et al., *Modulation of sleep by trimipramine in man*, European Journal of Clinical Pharmacol, 37: 145-150, (1989).
Kales et al., *Effects of Sinequan on sleep of Insomniac Subjects*, Sleep Study Abstracts, p. 93, (1972).
Hartmann et al., *The Effects of Long Term Administration of Psychotropic Drugs on Human Sleep: Ill. The Effects of Amitriptyline*, Psychopharmacologia, 33: 185-202 (1973).
Jacobsen, *Low-Dose Trazodone as a Hypnotic in Patients Treated with MAOIs and Other Psychotropics: A Pilot Study*, Journal of Clinical Psychiatry, 51: 298-392 (1990).
Gillin et al., *Successful Separation of Depressed, Normal, and Insomniac Subjects by EEG Sleep Data*, Arch Gen Psychiatry, vol. 36, p. 85-90, (1979).
German Federal Gazette (BAnz) No. 240 of Dec. 22, 1992, p. 9545 (vol. 44).
Dunleavy et al., *Changes During Weeks in Effects of Tricyclic Drugs on the Human Sleeping Brain*, British Journal of Psychiatry, 120: 663-672, (1972).
Conn et al., *Pattern of Use of Antidepressants in Long-Tem Care Facilities for the Elderly*, Journal of Geriatric Psychiatry and Neurology, vol. 5:4, p. 228-232, (1992).
ABPI (Association of the British Pharmaceutical Industry) Medicines Compendium, 2002; Pfizer Limited, p. 1792-1793.
ABPI (Association of the British Pharmaceutical Industry) Compendium of Data Sheets & SmPC's, 1999-2000; Pfizer Limited, p. 1158-1159.
ABPI (Association of the British Pharmaceutical Industry) Compendium of Data Sheets and Summaries of Product Characteristics, 1996-1997; Pfizer Limited, p. 751-752.
ABPI (Association of the British Pharmaceutical Industry) Data Sheet Compendium 1995-1996; Pfizer Limited, p. 1239-1240.
ABPI (Association of the British Pharmaceutical Industry) Data Sheet Compendium 1994-1995; Pfizer Limited, p. 1150-1151.
ABPI (Association of the British Pharmaceutical Industry) Data Sheet Compendium 1993-1994; Pfizer Limited, p. 1205-1207.
ABPI (Association of the British Pharmaceutical Industry) Data Sheet Compendium 1991-1992; Pfizer Limited, p. 1147-1149.
Chen, *Sleep, Depression and Antidepressants*, British Journal of Psychiatry, 135: 385-402, (1979).
Hajak et al., *Nocturnal Melatonin Secretion and Sleep after Doxepin Administration in Chronic Primary Insomnia*, Pharmacopsychiatry 29: 187-192, (1996).
National Academy of Sciences, *Sleeping Pills, Insomnia, and Medical Practice*, Institute of Medicine, 32-33,103,125,149,169,198, (1979).
Schatzberg et al., *"Hypnotics" Manual of Clinical Psychopharmacology*, American Psychiatric Press, Inc., Washington D.C., p. 173-189, (1986).
Seminar on Psychosomatics, *Auspices of* Academy of Psychosomatic Medicine, p. 4-63 (1968).
Pfizer, *Chemist Review of NNA 17-516, Division of Neurophamacological Drug Products, Chemists Review #3*, (1973).
Summary Basis for approval of ADAPIN (1972) Pursuant to FOIA Request filed in 1981.
Roth et al., *Psychopharmacolodgy: The Effects of Doxepin HCl on Sleep and Depression*, Journal of Clinical Psychiatry, 43:9, p. 366-368 (1982).
Lapp, *Chronic Fatigue Syndrome is a Real Disease*, North Carolina Family Physician, 43:1, (1992).
Roth et al., *Efficacy and Safety of doxepin 1, 3 , and 6mg in elderly adults with primary insomnia*, Sleep (Rochester),29: suppl. S (2006).
Hsu et al., *Low-Dose Doxepin in the treatment of primary insomnia*, Sleep, 28: suppl, p. A50, (2005).
Doxal. Lääkeopas. Retrieved Nov. 28, 2005 from http://www.coronaria.fi/www/mtv3/laakkeet.php?id=299.
Doxal. Lääkkeet. Retrieved Nov. 28, 2005 from http:www.tohtori.fi/laakkeet/tuote.php3?ID=412.
Pharmaca Fennica. Published by the Finnish Centre for Medicine Information (Lääketietokeskus); Ye R Doxal; 534-535 (2000).
Pharmaca Fennica. Published by the Finnish Centre for Medicine Information (Lääketietokeskus); SR Doxal; 830 (1995).
Pharmaca Fennica. Published by the Finnish Centre for Medicine Information (Lääketietokeskus); SR Doxal; (1992).
Pharmaca Fennica. Published by the Finnish Centre for Medicine Information (Lääketietokeskus); SR Doxal; 738 (1993).
Pharmaca Fennica. Published by the Finnish Centre for Medicine Information (Lääketietokeskus); SR Doxal; 714 (1991).
Pharmaca Fennica. Published by the Finnish Centre for Medicine Information (Lääketietokeskus); SR Doxal; 612-613 (1988).
Approval data of the German drug regulatory authorities. DIMDI: AMIS—Public Part (AJ29). German Institute of Medical Documentation and Information within the scope of the Federal Ministry of Health. Pfizer Pharma GmBH. Sinquan 10 mg; capsules, SINQUAN 100; capsules; Sinquan 100 mg; capsules, Sinquan 25 Intramuscular; solution; Sinquan 25 mg; capsules, Sinquan 50 mg; capsules, Sinquan 75 mg; capsules. Retrieved Nov. 16, 2005 from https://gripsdb.dimdi.de/session/0511161521292992047/13docs.htm.
Polish Drug Application for SINEQUAN 10 mg capsules. 01474/93. p. 1-4 with attached Annex in 4 pages.
Polish Drug Application for SINEQUAN 25 mg capsules. 01475/93. p. 1-4 with attached Annex in 4 pages.
New Drug Application 16-798 for SINEQUAN approved in 1978 (includes evaluation of insomnia indication on pp. 46-47, 54, 57, 59.
Baldrick, Pharmaceutical Excipient Development: The Need for Preclinical Guidance. Regul. Toxicol. Pharmacol., 32(2):210-8 (2000).
Becker, Pharmacologic and Nonpharmacologic Treatments of Insomnia, Neurol Clin., 23: 1149-1163 (2005).
Brunello et al., Effect of Some Tricyclic and Nontricyclic Antidepressants on [H]Imiipramine Binding and Serotonin Uptake in Rat Cerebral Cortex After Prolonged Treatment. Fundam Clin Pharmacol., 1: 327-333 (1987).
CBS.com, Ambien May Prompt Sleep-Eating; http://www.cbsnews.com/stories/2006/03/15/early show/health/ (2 pages).
Charman, Lipids, Lipophilic Drugs, and Oral Drug Delivery-Some Emerging Concepts. J Pharm Sci., 89(8): 967-78 (2000).
Claudino et al., Antidepressants for Anorexia Nervosa (Review). Cochrane Database Syst Rev., 1: 1-39 (2006).
Erman et al., Comparative Efficacy of Zolpidem and Temazepam in Transient Insomnia, Human Psychopharma Clin Exp., 16: 169-176 (2001).
Fava, Weight Gain and Antidepressants. J Clin Psychiatry., (61 Suppl) 11: 37-41 (2000).
Fulton et al., Assessment of the Antidepressant Activity of Dothiepin and its Metabolites by Preclinical Tests. J Affect Dis., 4: 261-269 (1982).
Heal et al., Comparative Pharmacology of Dothiepin, its Metabolites, and other Antidepressant Drugs. Drug Dev Res., 27: 121-135 (1992).
Higuchi et al., Pro-Drugs as Novel Delivery Systems, A.C.S. Symposium Series, American Chemical Society; vol. 14, (1975) Title Pages Only.
Hohagen et al., Treatment of Primary Insomnia with Trimipramine: An Alternative to Benzodiazepine Hypnotics? Eur Arch Psychiatry Clin Neurosci, 244(2): 65-72 (1994).
Krakowski, Seminar on Psychopharmacology—Auspices of Academy of Psychosomatic Medicine, Dec. 8-9, 1968 Freeport, Grand Bahama Island, Psychosomatics, pp. 7-63 (1968).
Laimer et al., Effect of Mirtazapine Treatment on Body Composition and Metabolism, J Clin Psychiatry, 67(3): 421-524 (2006).
Manning et al., Central Nervous System Effects of Meclizine and Dimenhydrinate: Evidence of Acute Tolerance to Antihistamines. J. Clin. Psychiatry, 32:996-1002 (1992).
Masaki et al., Involvement of Hypothalamic Histamine H1 Receptor in the Regulation of Feeding Rhythm and Obesity, Diabetes, 53(9): 2250-2260 (2004).
Masaki et al., The Hypothalamic H1 Receptor: A Novel Therapeutic Target for Disrupting Diurnal Feeding Rhythm and Obesity. Trends Pharmacol Sci., 27(5): 279-284, (2006).
Mercer et al., Dietary Induced Anorexia: A Review of Involvement of the Histominergic System, J Am Coll Nutr., 15(3): 223-230, (1996).

Narasimhachari et al., N-Alkylation of Secondary Amine Tricyclic Antidepressants as a General Method for Their Quantitation by GC-MS-SIM Technique. Analytical Lett., 12(B1): 77-88 (1979).
Newcomer et al., The Metabolic Effects of Antipsychotic Medications, Can J Psychiatry, 51(8): 480-491 (2006).
Ookuma et al., Evidence for Feeding Elicited Through Antihistaminergic Effects of Tricyclic Antidepressants in the Rat Hypothalamus. Psychopharmacology (Berl). 101(4): 481-485, (1990).
Orthen-Gambill, Antihistaminic Drugs Increase Feeding, While Histidine Suppresses Feeding in Rats, Pharmacol Biochem Behav., 31(1): 81-86, (1988).
Orthen-Gambill et al., Differential Effects of Psychotropic Drugs on Feeding in Rats: Is Histamine Blockade Involved? Pharmacol Biochem Behav., 36(4): 837-841 (1990).
Powell et al. Compendium of Excipients for Parenteral Formulations, PDA J Pharm Sci Technol. 52(2): 238-311 (1998).
Prakash et al. Deuterium Labelling of the Antidepressant Drug Doxepin for Disposition Studies in Human Subjects. J Lab Comp Radiopharma. 28(9): 1037-47 (1990).
Richardson et al., Tolerance to Daytime Sedative Effects of H1 Antihistamines. J Clin Psychopharmacol. 22(5): 511-515 (2002).
Richelson et al., Antagonism by Antidepressants of Neurotransmitter Receptors of Normal Human Brain in Vitro, J Pharmacol Exp Ther. 230(1): 94-102 (1984).
Roche, Bioreversible Carriers in Drug Design: Theory and Application, Pergamon Press: New York, (1987) Contents pages only.
Roth et al., Efficacy and Safety of Zolpidem-MR: A Double-Blind, Placebo-Controlled Study in Adults with Primary Insomnia, Sleep Med. 7(5): 397-406 (2006).
Saul, Stephanie, Study Links Ambien Use to Unconscious Food Forays, The New York Times http://www.nytimes.com/2006/03/14/health/14sleep.html (4 pages).
Schweitzer et al., Sleepiness and Performance During Three-Day Administration of Cetirizine or Diphenhydramine. J Allergy Clin Immunol. 94(4): 716-724 (1994).
Somaxon Pharmaeuticals Announces the Completion of Enrollment in a Phase II Study Evaluating S0-101 for the Treatment of Sleep Maintenance Insomnia in Adults, Somaxon Pharmaceuticals, p. 1, (Oct. 7, 2004).
Somaxon Pharmaceuticals Announces Presentation of Phase II Silenor® Data at the Associated Professional Sleep Societies Annual Meeting, Somaxon Pharmaceuticals, p. 1-2, (Jun. 20, 2006).
Somaxon Pharmaceuticals Provides Update on SILENOR® Development Program for the Treatment of Insomnia, Somaxon Pharmaeuticals, p. 1-5, (Jul. 19, 2006).
Voshaar et al., Zolpidem is not Superior to Temazepam with Respect to Rebound Insomnia: A Controlled Study. Eur Neuropsychopharmacol. 14(4): 301-306 (2004).
Wolfe, Antidepressant Withdrawal Reactions. Am Fam Physician. 56(2): 455-462, (1997).
International Search Report dated Jan. 24, 2008 in PCT/2007/012105, filed May 18, 2007.
International Search Report dated Jan. 24, 2008 in PCT/2007/012106, filed May 18, 2007.
International Search Report dated Dec. 10, 2007 in PCT/2007/016464, filed Jul. 20, 2007.
International Preliminary Report on Patentability dated Jan. 20, 2009 in PCT/US2007/016464, filed Jul. 20, 2007.
International Search Report dated Jun. 17, 2008 in PCT/2007/080492, filed Oct. 4, 2007.
International Search Report and Written Opinion dated Jan. 21, 2008 in PCT/US2007/012107, filed May 18, 2007.
Office Action dated Feb. 25, 2009 in U.S. Appl. No. 11/804,720, filed May 18, 2007.
Office Action dated Mar. 6, 2009 in U.S. Appl. No. 12/022,628, filed Jan. 30, 2008.
Office Action dated Mar. 9, 2009 in U.S. Appl. No. 12/022,788, filed May 18, 2007.
Adamczyk et al. "Quantitative determination of E- and Z-doxepin and E- and Z-desmethyldoxepin by high-performance liquid chromatography." Ther Drug Monit. 17(4):371-6 (1995).
Badenhorst et al. "Determination of doxepin and desmethyldoxepin in human plasma using liquid chromatography-tandem mass spectrometry." J Chromatogr B Biomed Sci Appl. 742(1):91-8 (2000).
Biggs et al. "Dosage schedule and plasma levels of doxepin and desmethyldoxepin." J Clin Psychiatry. 39(10):740-2 (1978).
Bogaert et al. "Plasma levels of the cis- and trans-isomers of doxepin and desmethyldoxepin after administration of doxepin to patients." Arzneimittelforschung. 31(1):113-5 (1981).
Brunswick et al. "Relationship between tricyclic antidepressant plasma levels and clinical response in patients treated with desipramine or doxepin." Acta Psychiatr Scand. 67(6):371-7 (1983).
Deuschle et al. "Doxepin and its metabolites in plasma and cerebrospinal fluid in depressed patients." Psychopharmacology (Berl). 131:19-22 (1997).
Dilger et al. "High-performance liquid chromatographic determination of trans-doxepin and desmethyldoxepin." Arzneimittelforschung. 38(10):1525-8 (1988).
Ereshefsky et al. "Pharmacokinetic factors affecting antidepressant drug clearance and clinical effect: evaluation of doxepin and imipramine—new data and review." Clin Chem. 34(5):863-80 (1988).
Faulkner et al. "Multiple-dose doxepin kinetics in depressed patients." Clin Pharmacol Ther. 34(4):509-15 (1983).
Faulkner et al. "Comparative assays for doxepin and desmethyldoxepin using high-performance liquid chromatography and high-performance thin-layer chromatography." J Pharm Sci. 72(10):1165-7 (1983).
Friedel et al. Relationship of blood levels of sinequan to clinical effects in the treatment of depression in aged patients. In. Mendels J, editor. Amsterdam: Excerpta Medica. p. 51-53 (1975).
Ghabrial et al. "Geometric isomerization of doxepin during its N-demethylation in humans." Drug Metab Dispos. 19(3):596-9 (1991).
Green, Douglas 0. "Clinical importance of doxepin antidepressant plasma levels." J Clin Psychiatry. 39(5):481-2 (1978).
Haritos et a. "Role of cytochrome P450 2D6 (CYP2D6) in the stereospecific metabolism of E- and Z-doxepin." Pharmacogenentics. 10(7):591-603 (2000).
Haritos et al. "Stereoselective measurement of E- and Z-doxepin and its N-desmethyl and hydroxylated metabolites by gas chromatography-mass spectrometry." J Chromatogr B Biomed Sci Appl. 736(1-2):201-8 (1999).
Hartter et al. "The N-demethylation of the doxepin isomers is mainly catalyzed by the polymorphic CYP2C19." Pharm Res. 19(7):1034-7 (2002).
Hrdina et al. "Cis- and trans-isomers of doxepin and desmethyldoxepin in the plasma of depressed patients treated with doxepin." Ther Drug Monit. 12(2):129-33 (1990).
Hrdina et al. "Antidepressant plasma levels and clinical response in depressed patients treated with oxaprotiline and doxepin." Int Clin Psychopharmacol. Jul;3(3):205-14 (1988).
Joyce et al. "Doxepin plasma concentrations in clinical practice. Could there be a pharmacokinetic explanation for low concentrations?" Clin Pharmacokinet. 10(4):365-70 (1985).
Kirchheiner et al. "Contributions of CYP2D6, CYP2C9 and CYP2C19 to the biotransformation of E- and Z-doxepin in healthy volunteers." Pharmacogenetics. 12(7):571-80 (2002).
Kline et al. Doxepin and Desmethyldoxepin Serum Levels and Clinical Response. In: Gottschalk LA MM, editor. Pharmacokinetics of psychoactive drugs: blood levels and clinical response. New York: Spectrum Press. p. 221-228 (1976).
Leucht et al. "Doxepin plasma concentrations: is there really a therapeutic range?" J Clin Psychopharmacol. 21(4):432-9 (2001).
Linnoila et al. "Clomipramine and doxepin in depressive neurosis. Plasma levels and therapeutic response." Arch Gen Psychiatry. 37(11):1295-9 (1980).
Midha et al. "Stereoselective pharmacokinetics of doxepin isomers." Eur J Clin Pharmacol. 42(5):539-44 (1992).
O'Brien et al. "GLC determination of doxepin plasma levels." J Pharm Sci. 65(7):1068-9 (1976).
Pinder et al. "Doxepin up-to-date: a review of its pharmacological properties and therapeutic efficacy with particular reference to depression." Drugs. 13(3):161-218 (1977).

Ribbentrop et al. Pharmacologic studies of doxepin, an antidepressive agent with centrally anticholinergic and sedative effects. Arzneimittelforschung. 15:863-67 (1965).

Rosseel et al. "Quantitative GLC determination of cis- and trans-isomers of doxepin and desmethyldoxepin." J Pharm Sci. 67(6):802-5 (1978).

Shu et al. "Identification of phenolic doxepin glucuronides from patient urine and rat bile." Drug Metab Dispos. 18(6):1096-9 (1990).

Shu et al. "The identification of urinary metabolites of doxepin in patients." Drug Metab Dispos. 18(5):735-41 (1990).

Sokoliess et al. "Separation of (Z)- and (E)-isomers of thioxanthene and dibenz[b,e]oxepin derivatives with calixarenes and resorcinarenes as additives in nonaqueous capillary electrophoresis." Electrophoresis. 24 (10):1648-57 (2003).

Virtanen et al. "Radioimmunoassay for doxepin and desmethyldoxepin." Acta Pharmacol Toxicol (Copenh). 47(4):274-8 (1980).

Ward et al. "Doxepin plasma levels and therapeutic response in depression: preliminary findings." J Clin Psychopharmacol. 2(2):126-8 (1982).

Wyatt et al. "Carbon$^{13}$ NMR of Z- and E-Doxepin Hydrochloride." Applied Spectroscopy. 49(4):538-542 (1986).

Yan et al. Stereoselective in vivo and in vitro studies on the metabolism of doxepin and N-desmethyldoxepin. Xenobiotica. 27(12):1245-1257 (1997).

"Stereoselective and simultaneous measurement of cis- and trans-isomers of doxepin and N-desmethyldoxepin in plasma or urine by high-performance liquid chromatography." J Chromatogr B Biomed Sci Appl. 691(1):131-8 (1997).

Ziegler et al. "Doxepin kinetics." Clin Pharmacol Ther. 23(5):573-9 (1978).

Abernethyl et al., "Absolute bioavailability of imipramine: Influence of food," *Psychopharmacology* (Berl), 1984; 83(1):104-106.

Burch et al., "Amitriptyline pharmacokinetics. A crossover study with single doses of amitriptyline and nortriptyline," *Psychopharmacology* (Berl), 1981; 74(1):35-42.

Drugs & Medications—Sominex Oral. WebMD. Web. Jul. 6, 2010. http://www.webmd.com/drugs/drug-15470-Sominex+Oral. aspx?drugid=15470&drugname=Sominex+Oral&source=1.

Drugs & Medications—Nytol Oral. WebMD. Web. Jul. 6, 2010. http://www.webmd.com/drugs/drug-10538-Nytol+Oral. aspx?drugid=10538&drugname=Nytol+Oral&source=0.

Drugs & Medications—Tylenol PM Oral. WebMD. Web. Jul. 6, 2010. http://www.webmd.com/drugs/drug-74986-Tylenol+PM+Oral.aspx?drugid=74986&drugname=Tylenol+PM+Oral&source=1.

Drugs & Medications. NyQuil Oral. WebMD. Web. Jul. 6, 2010. http://www.webmd.com/drugs/drug-6104-NyQuil+Oral. aspx?drugid=6104&drugname=NyQuil+Oral&source=1.

Chloral Hydrate Drug Information, Professional. Chloral Hydrate (Systemic). Drug Information Online. Drugs.com. Web. Jul. 6, 2010. http://www.drugs.com/mmx/chloral-hydrate.html.

SINEQUAN (doxepin HCl) Capsules Concentrate. Prescribing Information. Revised Oct. 2008.

Sinequan Dosage. eMEDTV. Clinaero, Inc. Updated/reviewed Apr. 2, 2007. Web. Jul. 6, 2010. http://depression.emedtv.com/sinequan/sinequan-dosage.html.

Sinequan (Doxepin, Adapin): A guide to sinequan side effects. depression-guide.com. (2005). Web. Jul. 6, 2010. http://www.depression-guide.com/sinequan.htm.

Doxepin. Find Treatment & Support. The most reliable cancer treatment information. Cancer.org. Web. Jul. 6, 2010. http://www.cancer.org/docroot/CDG/content/CDG_doxepin.asp?internal=1.

Ambien CR (zolpidem tartrate extended release). Healthcare Professional Information. Healthcare Professionals. Help your insomnia patients meet the day on. Web. Jul. 6, 2010. http://www.ambiencr.com/hcp/zolpidem-tartrate.aspx.

Ambien CR (zolpidem tartrate extended release) tablets—CIV. Full Prescribing Information. Sep. 2009. Web. Jul. 6, 2010. http://products.sanofi-aventis.us/ambien_cr/ambiencr.html.

Silenor (doxepin) Prescribing Information. Revised Mar. 2010.

Restoril-temazepam capsule. Mallinckrodt Inc. Prescribing Information. Revised Mar. 2006.

Halcion—triazolam tablet. Pharmacia and Upjohn Company. Prescribing Information. Revised Jan. 2009.

Ambien (zolpidem tartrate) tablets CIV. Prescribing Information. Revised Jun. 2009.

Sinequan (doxepin HCL) Capsules Oral Concentrate. Prescribing Information. Revised Oct. 2008.

Elavil—Amitriptyline Hydrochloride—amitriptyline hydrochloride tablet, film coated. Mutual Pharmceutical Company, Inc. Revised Sep. 2007.

Desyrel—trazadone hydrochloride tablet. Bristol-Myers Squibb Company. Prescribing Information. Revised Feb. 2009.

Lunesta (eszopiclone) Tablets 1 mg, 2 mg, 3 mg. Prescribing Information. Sepracor Inc. Jan. 2009.

Rozerem (ramelteon) tablets. Prescribing Information. Revised Oct. 2008.

Sonata (zaleplon) Capsules. Prescribing Information. King Pharmaceuticals. Feb. 2009.

Sonata Official FDA information, side effects and uses. Drug Information Online. Drugs.com. Web. Jul. 6, 2010. http://www.drugs.com/pro/sonata.html#ixzz0qJhTt6kd.

ABPI (Assoication of the British Pharmaceutical Industry) Data Sheet Compendium of Data Sheets and Summaries of Product Characteristics 1998-1999; Pfizer Limited. p. 970-971.

Fawcett, et al., "Review of the results form clinical studies on the efficacy, safety and tolerability of mirtazapine for the treatment of patients with major depression" *J. Affective Disorders* (1998) 51: 267-285.

Georgotas, et al., "Response of Depressive Symptoms to Nortiptyline, Phenelzine and Placebo" *Br. J. Psychiatry* (1987) 151: 102-106.

Hartmann, Peter M., "Miratzapine: A Newer Antidepressant" *American Family Physician* (1999) 1-5.

*Physician's Desk Reference*, 1999 ed., Medical Economics Company, Montvale NJ pp. 539-541 (trazadone).

*Physician's Desk Reference*, 2000 ed., Medical Economics Company, Montvale NJ pp. 3323-3324 (trimipramine maleate).

*Physician's Desk Reference*, 2000 ed., Medical Economics Company, Montvale NJ pp. 549-551 (Amitriptyline HCl).

*Physician's Desk Reference*, 2000 ed., Medical Economics Company, Montvale NJ pp. 2366-2367 (Doxepine HCl).

Pollack, Andrew, "Is Biotechnology Losing Its Nerve?" *NY Times* (Feb. 29, 2004).

Somaxon Pharmaceuticals Announces the Completion of Enrollment in a Phase II Study Evaluating S0-101 for the Treatment of Sleep Maintenance Insomnia in Adults, Somaxon Pharmaceuticals Press Release, San Diego, CA (Oct. 7, 2004).

Somaxon Pharmaceuticals Announces positive Results in a Phase II Dose-Finding Study of Low-dose Doxepin in Adults with Primary Sleep Maintenance Insomnia, Somaxon Pharmaceuticals Press Release, San Diego, CA (Jan. 6, 2005).

Somaxon Pharmaceuticals Announces Positive Results in a Phase II Dose-Finding of Low-Dose Doxepin in Elderly Patients with Primary Sleep Maintenance Insomnia, Somaxon Pharmaceuticals Press Release, San Diego, CA (Apr. 21, 2005).

Somaxon Pharmaceuticals, Inc. Initiates Phase III Clinical Trials of SILENOR™ in Patients with Insomnia, Somaxon Pharmaceuticals Press Release, San Diego, CA (Jun. 9, 2005).

Somaxon Pharmaceuticals, Inc. Initiates Second Phase III Clinical Trials of SILENOR™, Somaxon Pharmaceuticals Press Release, San Diego, CA (Sep. 20, 2005).

Somaxon Pharmaceuticals, Announces presentation of Phase 2 SILENOR™ Data at the Associated Professional Sleep Societies Annual Meeting, Somaxon Pharmaceuticals Press Release, San Diego, CA (Jun. 20, 2006).

Somaxon Pharmaceuticals Provides Update on SILENOR™ Development Program for the Treatment of Insomnia, Somaxon Pharmaceuticals Press Release, San Diego, CA (Jul. 19, 2006).

Somaxon Pharmaceuticals Provides Update on Preclinical and Clinical Programs for SILENOR™, Somaxon Pharmaceuticals Press Release, San Diego, CA (Sep. 11, 2006).

Somaxon Pharmaceuticals' SILENOR™ Demonstrates Positive Results in a Phase 3 Transient Insomnia Clinical Trial, Somaxon Pharmaceuticals Press Release, San Diego, CA (Oct. 23, 2006).

Somaxon Pharmaceuticals' SILENOR™ Demonstrates Positive Results in its Third Phase 3 Clinical Trial in Insomnia, Somaxon Pharmaceuticals Press Release, San Diego, CA (Nov. 20, 2006).

Somaxon's SILENOR™ Demonstrates Positive Results in Long-Term Phase 3 Clinical Trial in Elderly Patients with Insomnia, Somaxon Pharmaceuticals Press Release, San Diego, CA (Dec. 18, 2006).

Somaxon Provides Update on SILENOR™ Preclinical Program, Somaxon Pharmaceuticals Press Release, San Diego, CA (Feb. 13, 2007).

Somaxon Pharmaceuticals Provides Update on SILENOR™ Development Program, Somaxon Pharmaceuticals Press Release, San Diego, CA (May 9, 2007).

Somaxon Pharmaceuticals Announces Completion of 26-Week Transgenic Mouse Carcinogenicity Study of SILENOR™, Somaxon Pharmaceuticals Press Release, San Diego, CA (Jan. 9, 2008).

Somaxon Pharmaceuticals Submits New Drug Application for SILENOR™ for the Treatment of Insomnia, Somaxon Pharmaceuticals Press Release, San Diego, CA (Jan. 21, 2008).

Somaxon Pharmaceuticals Announces Acceptance for Filing of New Drug Application for SILENOR™ for the Treatment of Insomnia, Somaxon Pharmaceuticals Press Release, San Diego, CA (Apr. 15, 2008).

Somaxon Pharmaceuticals Announces Data to be Presented at American Psychiatric Association 161st Annual Meeting, Somaxon Pharmaceuticals Press Release, San Diego, CA (May 2, 2008).

Clinical Data on Somaxon Pharmaceuticals' Product Candidate for the Treatment of Insomnia Presented at American Psychiatric Association Annual Meeting, Somaxon Pharmaceuticals Press Release, San Diego, CA (May 7, 2008).

Somaxon Pharmaceuticals to Present Data at the 22nd Annual Meeting of the Associated Professional Sleep Societies, Somaxon Pharmaceuticals Press Release, San Diego, CA (Jun. 4, 2008).

SILENOR™ Data Presented at the 22nd Annual Meeting of the Associated Professional Sleep Societies, Somaxon Pharmaceuticals Press Release, San Diego, CA (Jun. 12, 2008).

Somaxon Presents Pharmacological Data on Doxepin at the 21st European College of Neuropsychopharmacology Congress, Somaxon Pharmaceuticals Press Release, San Diego, CA (Sep. 2, 2008).

Somaxon Receives Complete Response Letter from the FDA for SILENOR® (Doxepin), Somaxon Pharmaceuticals Press Release, San Diego, CA (Feb. 26, 2009).

Somaxon Provides Update on New Drug Application for SILENOR® (Doxepin) for the Treatment of Insomnia, Somaxon Pharmaceuticals Press Release, San Diego, CA (Apr. 7, 2009).

Somaxon Pharmaceuticals Presents Analyses of Silenor Clinical Data at the American Psychiatric Association Annual Meeting, Somaxon Pharmaceuticals Press Release, San Diego, CA (May 20, 2009).

Somaxon Resubmits New Drug Application for SILENOR® (Doxepin) for the Treatment of Insomnia, Somaxon Pharmaceuticals Press Release, San Diego, CA (Jun. 4, 2009).

Somaxon Receives Complete Response Letter from the FDA for SILENOR® NDA, Somaxon Pharmaceuticals Press Release, San Diego, CA (Dec. 7, 2009).

Somaxon Scheduled to Meet with FDA to Discuss Complete Response Letter for SILENOR® NDA, Somaxon Pharmaceuticals Press Release, San Diego, CA (Dec. 17, 2009).

Somaxon Provides Update on New Drug Application for SILENOR® for the Treatment of Insomnia, Somaxon Pharmaceuticals Press Release, San Diego, CA (Jan. 21, 2010).

Somaxon Announces FDA Approval of SILENOR® (Doxepin) for the Treatment of Insomnia, Somaxon Pharmaceuticals Press Release, San Diego, CA (Mar. 18, 2010).

Somaxon Pharmaceuticals Announces Positive Phase 3 Results with SILENOR™ for the Treatment of Adults with Chronic Insomnia, Somaxon Pharmaceuticals Press Release, San Diego, CA (Apr. 10, 2006).

Stimmel, et al., "Mirtazapine: An Antidepressant with Noradrenergic and Specific Serotonergic Effects" *Pharmacotherapy* (1997) 17(1): 10-21.

Summary Basis for Approval of SINEQUAN (1973); Pursuant to FOIA Request filed in 1996 (sedative, tranquilizer and sleep effects mentioned for example on pags. 50, 54-56, 58-59).

Thase, Michael E., "Antidepressant Treatment of the Depressed Patient with Insomnia" *J. Clin. Psychiatry* (1999) 60(Suppl. 17): 28-31.

Vincent, et al., "Utilisation du Sommeil Humain comme Test de L'Action Psychotrope d'un Medicament Exemple: La Doxepine" *Bordeaux Medical* (1971) 16: 2651-2658. (English Translation).

Office Action dated Nov. 30, 2009 in U.S. Appl. No. 11/804,720, filed May 18, 2007.

* cited by examiner

US 7,915,307 B2

METHODS OF IMPROVING THE PHARMACOKINETICS OF DOXEPIN

CROSS-REFERENCE TO RELATED APPLICATIONS

This application claims priority to U.S. Provisional Application Nos. 60/832,727 and 60/833,617, respectively filed on Jul. 20, 2006 and Jul. 24, 2006, both entitled METHODS OF IMPROVING THE PHARMACOKINETICS OF DOXEPIN. The disclosure of each of the above-described applications is hereby incorporated by reference in its entirety.

FIELD OF THE INVENTION

The present invention relates to methods of improving the pharmacokinetics of doxepin in a patient.

BACKGROUND OF THE INVENTION

The term "food effect" refers to a somewhat unpredictable phenomenon that can influence the absorption of drugs from the gastrointestinal tract following oral administration. A food effect can be designated "negative" when absorption is decreased, or "positive" when absorption is increased and manifested as an increase in oral bioavailability (as reflected by total exposure, usually defined as AUC). Alternatively, food effects can refer to changes in maximum concentration ($C_{max}$), or the time to reach maximum concentration ($T_{max}$), independently of overall absorption. As a result, some drugs have to be taken in either fasted or fed conditions to achieve the optimum effect. For example, patients may be instructed to take a drug with a meal, before a meal (e.g., one hour before a meal), or after a meal (e.g., two hours after a meal). However, many drugs are unaffected by food, and thus, can be taken in either a fasted or a fed condition.

Doxepin is a tricyclic compound currently approved for treatment of depression and anxiety. The recommended daily oral dose for the treatment of depression or anxiety ranges from 75 milligrams to 300 milligrams. Also, U.S. Pat. Nos. 5,502,047 and 6,211,229 describe the use of doxepin for the treatment chronic and non-chronic (e.g., transient/short term) insomnia. Doxepin, unlike most FDA-approved products for the treatment of insomnia, is not a Schedule IV controlled substance. Historically, doxepin pharmacokinetics have not been known to be affected by food.

In treating depression, anxiety and sleep disorders it is beneficial to optimize the pharmacokinetics of the administered medication in a patient. For example, in the case of sleep disorders a patient may have a set window of time within which they desire that their sleep occur. Thus, it can be useful to minimize the amount of time required to attain a maximum concentration of a drug in order to receive the therapeutic benefit of the drug as soon as possible during the desired treatment period.

SUMMARY OF THE INVENTION

Some embodiments are based upon the surprising discovery about the food effects of doxepin. For example, as described more fully below, it has been discovered that administration of doxepin without food decreases the time to achieve maximum blood concentration or $T_{max}$ for doxepin. In one experiment, the administration of doxepin without food resulted in achieving $T_{max}$ three hours more quickly than when doxepin was administered with food. As another example, it has been discovered that administration of doxepin with food increases the overall bioavailability of doxepin and results in a higher maximum concentration ($C_{max}$) of doxepin. In one experiment, the administration of doxepin with food resulted in a 41% increase in bioavailability ($AUC_{0-\infty}$) and a 15% increase in $C_{max}$ compared to administration in a fasted state.

As a result of the various discoveries related to the food effects of doxepin and depending upon the type of therapy and the desired overall result of that therapy, a patient can benefit from a number of different therapeutic regimens. Disclosed are various therapeutic regimens influenced by the food effects observed with doxepin.

Achieving a More Rapid Maximum Concentration ($T_{max}$)

In some circumstances, more rapid onset of doxepin action may be desired. One embodiment relates to a method of shortening the time required to achieve a maximum plasma concentration of doxepin in a patient receiving doxepin therapy, which method can include administering to the patient a therapeutically effective amount of doxepin in a pharmaceutical composition without food. The methods can have various benefits, including more rapid onset of drug action, shorter duration of effect, etc. The administration to the patient can occur, for example, at least about 30 minutes, at least about 1 hour, at least about 2 hours, at least about 3 hours or at least about 4 hours, or more after consuming food. Also, administration to the patient can occur at least about 30 minutes, at least about 1 hour, at least about 2 hours, at least about 3 hours, or at least about 4 hours, or more prior to consuming food, for example.

Sleep Therapy:

Another embodiment relates to methods of treating sleep disorders. A desirable sleep medication preferably can have the ability to affect the onset of drug action and the duration of drug activity (e.g., to avoid hangover, etc.). Generally, a person will desire to fall asleep as soon as possible, to stay asleep for about 8 hours, and to wake up without hangover or extra sedation at the end of the 8 hours. As mentioned above, surprisingly, the administration of doxepin without food resulted in achieving a maximum concentration of the drug three hours sooner compared to administration with food. As a result, when treating sleep, doxepin can be taken without food in order to achieve earlier onset of drug action and/or a shorter duration of drug action.

Thus, some embodiments relate to a method of shortening the time required to achieve sleep onset, which method can include administering to the patient a therapeutically effective amount of doxepin in a pharmaceutical composition without food. Also, another embodiment relates to a method of treating a sleep disorder comprising providing a patient with a therapeutically effective amount of doxepin and providing the patient with instructions to take the doxepin without food. The doxepin can be provided to the patient at least about 30 minutes, at least about 1 hour, at least about 2 hours, at least about 3 hours or at least about 4 hours or more after consuming food, or at least about 30 minutes, or at least about 1 hour prior to consuming food.

Still a further embodiment relates to a method of treating a sleep disorder comprising providing a patient with a therapeutically effective amount of doxepin and providing the patient with information regarding a doxepin food effect. The information can be provided orally or in written form. Some exemplary written forms include a label associated with the drug, on the container for the drug, packaged with the drug, or separately given to the patient apart from the drug.

Still some embodiments relate to the use of doxepin in the preparation of a medicament for treatment of a sleep disorder, said medicament for administration without food. Also, the use can further be for shortening the time required to achieve a maximal plasma concentration of doxepin by administration without food. The administration without food can occur when the patient is in a fasted state. The administration without food can occur, for example, at least about 30 minutes, at least about 1 hour, at least about 2 hours, at least about 3 hours or at least about 4 hours, or more after consuming food. Also, it can occur, for example, at least about 30 minutes, at least about 1 hour, at least about 2 hours, at least about 3 hours, or at least about 4 hours, or more prior to consuming food. In some aspects, the administration of the doxepin can occur, for example, at least about 30 minutes, at least about 1 hour, or more prior to consuming food.

Achieving a Greater $C_{max}$ or a Greater Bioavailability

Greater $C_{max}$:

Some embodiments relate to a method of increasing the maximum plasma concentration of doxepin in a patient receiving doxepin therapy comprising administering to the patient a therapeutically effective amount of doxepin in a pharmaceutical composition with food.

Greater Bioavailability:

Also, some embodiments relate to methods of increasing the oral bioavailability of doxepin, including by administering to a patient an amount of a pharmaceutical oral dosage form of doxepin with food. Further embodiments relate to methods of increasing the oral bioavailability of doxepin to a patient receiving doxepin therapy, which methods can include administering to the patient an amount of a pharmaceutical oral dosage form of doxepin with food, wherein the administration results in an $AUC_{0-\infty}$ that is greater than that achieved by the administration of the same amount of doxepin without food. In such methods, the doxepin can be administered as part of a chronic doxepin therapy, for example.

Anxiety/Depression Therapy:

Still another embodiment relates to methods of treating depression or anxiety. It is worth noting that improved pharmacokinetics of doxepin in the context of depression or anxiety can be beneficial, for example by, leading to more safe and effective dosing. The methods of treating depression or anxiety can include administering a therapeutically effective amount of doxepin preferably with food. In some embodiments the depression or anxiety can be treated by administering doxepin without food. Also, some embodiments relate to methods of treating depression or anxiety, including by providing a patient with a therapeutically effective amount of doxepin and providing the patient with instructions to preferably take the doxepin with food. In some alternative embodiments, the instructions can specify taking the doxepin without food.

Another embodiment relates to a method of treating depression or anxiety comprising providing a patient with a therapeutically effective amount of doxepin and providing the patient with information regarding a doxepin food effect.

Also, some embodiments relate to the use of doxepin in the preparation of a medicament for treatment of a psychological disorder, said medicament for administration with food. The disorder can preferably be depression or anxiety. The use also can be for the preparation of a medicament for increasing the oral bioavailability of doxepin by administration with food; for increasing the oral bioavailability of doxepin to a patient receiving doxepin therapy by administering an amount of a pharmaceutical oral dosage form of doxepin with food, wherein the administration results in an $AUC_{0-\infty}$ that is greater than that achieved by the administration of the same amount of doxepin without food; for increasing the time required to achieve a maximal plasma concentration of doxepin by administration with food; for minimizing side effects associated with a doxepin treatment of the psychological disorder, by administering a therapeutically effective amount of doxepin with food, which can result in the patient receiving or in a physician prescribing a lower dosage of doxepin compared the dosage that is taken by the patient without food; or for improving the consistency of pharmacokinetics associated with doxepin therapy, in which a patient receives a multiple doxepin dosages over multiple days, comprising administering the doxepin in a fixed temporal relationship to food intake by the patient.

Decreasing Bioavailability:

It should be noted that some embodiments relate to methods of decreasing the oral bioavailability of doxepin. Decreasing oral bioavailability can be beneficial in some contexts. For example, as mentioned above for sleep therapies, it can be beneficial to shorten the duration of the drug action in order to minimize hangover or other effects. The methods of decreasing bioavailability can include administering to a patient an amount of a pharmaceutical oral dosage form of doxepin without food. Furthermore, some embodiments relate to methods of decreasing the oral bioavailability of doxepin to a patient receiving doxepin therapy, comprising administering to the patient an amount of a pharmaceutical oral dosage form of doxepin without food, wherein the administration results in an $AUC_{0-\infty}$ that is less than that achieved by the administration of the same amount of doxepin with food. In such methods, doxepin can be administered as part of a chronic doxepin therapy, for example. Also, in such methods administration to the patient can occur, for example, at least about 30 minutes, at least about 1 hour, at least about 2 hours, at least about 3 hours or at least about 4 hours, or more after consuming food. Also, administration to the patient can occur at least about 30 minutes, at least about 1 hour, at least about 2 hours, at least about 3 hours, or at least about 4 hours, or more prior to consuming food, for example.

Minimizing Doxepin Side Effects and Improving Pharmacokinetic Consistency

Some embodiments relate to methods of minimizing side effects associated with a doxepin therapy. The methods can include, for example, administering a therapeutically effective amount of doxepin to a patient with food. Also, the administration of doxepin with food can result in a patient receiving or a physician prescribing a lower dose of doxepin compared to the dosage prescribed without food.

This disclosure includes a method for improving the consistency of pharmacokinetics associated with doxepin therapy, in which a patient receives multiple doxepin dosages over multiple days, comprising administering the doxepin to the patient in a fixed temporal relationship to food intake by the patient. This can, for example, include providing written or verbal instructions to the patient to take the doxepin in a fixed temporal relationship to food intake by the patient. Taking doxepin in a fixed relationship to food can help assure more consistent efficacy of the medication.

Other Food Effect Methods

Also, some embodiments relate to methods of alleviating a doxepin food effect or altering a doxepin pharmacokinetic parameter in a patient, for example, by administering doxepin to a patient in need thereof, wherein the patient is in a non-fasted state or in a fasted state.

Further embodiments relate to a method of treating a disorder with doxepin comprising providing a patient with a therapeutically effective amount of doxepin and providing the patient with information regarding a doxepin food effect. The information can include, for example, instructions to take the doxepin with or without food, or to ensure that doxepin is consistently taken either with or without food. The information can be in an oral or written form. Some exemplary written forms include a label associated with the drug, on the container for the drug, packaged with the drug, separately given to the patient apart from the drug, or provided in manner that the patient can independently obtain the information (e.g., a website).

Dosage and Compositions

Again, in the various disclosed embodiments, the amount of doxepin, including the therapeutically effective amount, may advantageously be, for example, about 0.001 milligram to about 350 milligrams, preferably about 50 milligrams to about 300 milligrams or more preferably about 75 milligrams to about 300 milligrams, or any amount or sub-range within those ranges. Alternatively, the effective amount may be about 0.5 milligrams to about 20 milligrams, more preferably about 1 milligram to about 6 milligrams.

Also, in the various disclosed embodiments, the pharmaceutical composition of doxepin can be, for example, a tablet, capsule or liquid. Furthermore, the doxepin can be provided or administered as a unit dosage form. Preferably, the doxepin can be provided or administered as an oral dosage form.

Doxepin Kits and Products

Finally, the present disclosure also includes a kit or a product that includes doxepin and written instructions or information associated therewith to take the doxepin without food. For example, the instructions can specify that doxepin be administered to the patient at least about 30 minutes, at least about 1 hour, at least about 2 hours, at least about 3 hours, at least about 4 hours or more after consuming food, or at least about 30 minutes, at least about 1 hour, at least about 2 hours, at least about 3 hours, at least about 4 hours or more prior to consuming food, for example. In some aspects, the kits or product can include instructions that describe administration to the patient preferably at least about 30 minutes or at least about 1 hour prior to consuming food. The kit or product can include information regarding a food effect associated with doxepin. Alternatively, it includes a kit or a product comprising doxepin and written instructions associated therewith to take the doxepin with food.

The product or kit can include doxepin in amount of about 0.5 milligram to about 350 milligrams, preferably about 50 milligrams to about 300 milligrams or more preferably about 75 milligrams to about 300 milligrams. Alternatively, the amount may be about 0.5 milligrams to about 20 milligrams, more preferably about 1 milligram to about 6 milligrams. Some preferred amounts are about 1 milligram, about 3 milligrams and about 6 milligrams.

Finally, the product or kit can include doxepin as a tablet, a capsule, a liquid, a unite dosage form or an oral dosage form, for example.

DETAILED DESCRIPTION OF THE INVENTION

Figure 1:
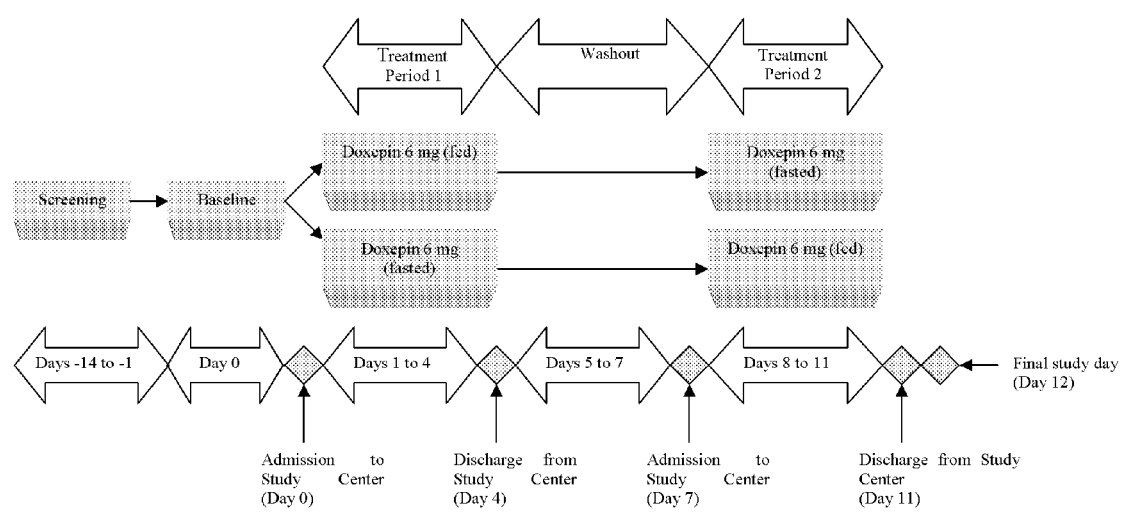
FIG. 1 illustrates the design of a study of food effect associated with doxepin.

Embodiments described herein relate to the novel and unexpected discovery of a food effect associated with doxepin. As described more fully below, a single-center, phase 1, randomized, open-label, single dose, two-way crossover study was conducted in 16 healthy young adult male and female volunteers. A food effect was observed on the pharmacokinetics of doxepin. In the fed state, pharmacokinetic parameters ($AUC_{0-\infty}$ and $C_{max}$) of doxepin were approximately 41% and 15% higher, respectively, compared to the fasted state, and median $T_{max}$ was delayed by approximately 3.0 hours in the fed state. The increase in AUC was statistically significant and demonstrates a positive food effect on exposure. The increased $T_{max}$ in the fed state suggests that food slows the absorption of the drug.

Accordingly, some embodiments relate to methods of improving the pharmacokinetics of doxepin in a patient. As discussed above and more fully elsewhere herein, administration of doxepin in a fasted state can result in decreasing the time required to achieve a maximum plasma concentration of doxepin. In particular, the time to reach maximum concentration ($T_{max}$) of doxepin can be minimized by administering the drug without food. Also, as discussed above and more fully elsewhere herein, administration of doxepin with food can increase the overall bioavailability of the drug. For example, the time to reach maximum concentration can be increased by administering doxepin with food and the bioavailability of the drug can be increased.

In addition, in a different embodiment, the total effective amount of drug that the patient receives can be maximized by administering doxepin with food, while in other embodiments the oral bioavailability of doxepin can be decreased by administering the doxepin without food. Because plasma concentrations and half-lives of doxepin are already known to vary from patient to patient, knowledge of the doxepin food effect can help patients and physicians to eliminate this additional source of dosing uncertainty, to improve safety and tolerability, and improve therapies that utilize doxepin. For example, as described more fully elsewhere herein, depending on the effect desired, doxepin can be taken with food; it can be taken after the patient has gone without food for a period of time; and/or it can be taken some period of time prior to consuming food.

As a result of the food effect discovery, various improved therapeutic methods are provided, including: where short term exposure is desired, with a more rapid onset and shorter duration of effect, doxepin preferably can be taken without food; in order to increase the bioavailability of the drug where rapid onset and shorter duration are not issues, doxepin preferably can be taken with food; and to assure more consistent efficacy, doxepin preferably can be taken in a fixed relationship to food consumption, regardless of whether the drug is taken with our without food. Short term exposure with more rapid onset can be preferable when treating, for example, a sleep disorder, while increased bioavailability and/or consistent kinetics can be preferable for treating conditions such as depression and anxiety.

Doxepin HCl is a tricyclic compound currently approved for treatment of depression and anxiety. The recommended daily dose for the treatment of depression or anxiety ranges from 75 milligrams to 300 milligrams. Also, U.S. Pat. Nos. 5,502,047 and 6,211,229, the entire contents of which are incorporated herein by reference, describe the use of doxepin for the treatment chronic and non-chronic (e.g., transient/short term) insomnias at dosages below those used to treat depression. A food effect associated with doxepin treatment of currently approved disorders or sleep disorders has not previously been reported.

Methods of Improving the Pharmacokinetics of Doxepin

Some embodiments relate to methods of improving the pharmacokinetics of doxepin, including by administering doxepin with or without food. A number of pharmacokinetic parameters can be affected by taking doxepin with or without food, including for example, $T_{max}$, $C_{max}$, and the area under the curve (AUC). Furthermore, various therapeutic regimens can be utilized to take advantage of the doxepin food effects.

Affecting Maximum Concentration ($T_{max}$):

As discussed above, administration of doxepin without food or in a fasted state can result in shortening the time required to achieve a maximum plasma concentration ($T_{max}$) of doxepin. Achieving a shorter $T_{max}$ can be desirable since onset of drug action can be more rapid and the duration of drug action may be shortened. Some embodiments relate to methods of shortening the time required to achieve a maximum plasma concentration or a $T_{max}$ of doxepin in a patient receiving doxepin therapy, which methods can include administering to the patient a therapeutically effective amount of doxepin in a pharmaceutical composition without food.

Also, it should be noted that other embodiments relate to methods of increasing the time required to achieve a maximum concentration of doxepin in a patient by administering doxepin with food.

Some embodiments relate to methods of preventing a doxepin food effect in order to minimize the time required for onset of action of the drug. The methods can include administering doxepin to a patient in need thereof, wherein the patient is in a fasted state or has not eaten or will not eat within a particular time period. The methods further can include providing instructions to take the doxepin without food or in a fasted state.

Use of Doxepin in Sleep-Related Indications:

Knowledge of the food effect disclosed herein is useful in determining an optimum regimen for providing doxepin sleep therapy. In patients receiving sleep therapy, the onset of action is an important consideration. The studies disclosed herein demonstrate that taking doxepin with food can significantly increase $T_{max}$. As a result, sleep patients who take doxepin without food would be expected to have faster sleep onset or faster drug action in comparison to those who take doxepin with food.

Thus, some embodiments relate to improved methods of treating a sleep disorder. The methods can include providing a patient with a therapeutically effective amount of doxepin and providing the patient with instructions to take the doxepin without food. In some aspects, doxepin can be administered without food in order to minimize the amount of time to achieve sleep onset or to otherwise minimize the amount of time before drug action occurs.

The information regarding the doxepin food effect can be provided to the patient. The information can include, for example, instructions that may be provided to patients receiving doxepin therapy or health care professionals involved in treatment of those patients that the doxepin should be administered without food, preferably separated from food for the time periods discussed above. By way of example, such instructions could be provided orally or in written form. Some exemplary written forms include a label associated with the drug, on the container for the drug, packaged with the drug, or separately given to the patient apart from the drug, including providing the patient with access to a website or other electronic information with the instructions/information.

Affecting Overall Concentration ($C_{max}$) or Bioavailability:

The maximum plasma concentration or overall bioavailability of doxepin can be affected by food or a lack thereof. Increasing concentration or bioavailability can be desirable in some circumstances. Some embodiments relate to methods of increasing the oral bioavailability of doxepin to a patient receiving doxepin therapy. The methods can include administering to the patient a pharmaceutical oral dosage form of doxepin with food. The administration can result in a greater AUC than if the drug is taken without food. The methods can include administering to the patient a therapeutically effective amount of doxepin in a pharmaceutical composition with food or within a relatively short time of consuming food (e.g., 15 minutes, 30 minutes, one hour, etc.).

Also, some embodiments relate to a method of increasing the maximum plasma concentration of doxepin in a patient receiving doxepin therapy comprising administering to the patient a therapeutically effective amount of doxepin in a pharmaceutical composition with food.

It should be noted that other embodiments relate to methods of decreasing the oral bioavailability or AUC of doxepin by administering doxepin without food.

Use of Doxepin in Depression and Anxiety:

Doxepin has been used for several decades in the treatment of depression and anxiety. Several side effects have been reported in connection with the use of doxepin to treat depression or anxiety. The studies disclosed herein show that by taking doxepin with food, AUC was increased by 41% compared to taking doxepin in a fasted state. Because AUC (bioavailability) is increased by taking doxepin with food, a patient can take a lower dose compared to when a patient takes doxepin without food. Increasing the oral bioavailability or AUC of doxepin, and decreasing dosage required for treatment can minimize or alleviate side effects and improve the safety and tolerability of doxepin therapy. Thus, in some aspects it can be preferred that patients receiving doxepin for depression or anxiety should take the drug with food, or in close proximity to eating. Some embodiments relate to improved methods of treating depression and anxiety. The methods can include providing a patient with a therapeutically effective amount of doxepin and providing the patient with instructions to take the doxepin with food. As discussed more fully herein, administering doxepin with food can result in an increase in the bioavailability of doxepin. As a result a patient can take less doxepin, which can be safer and more tolerable for the patient.

In some aspects, information, including instructions may be provided to patients receiving doxepin therapy or health care professionals involved in treatment of those patients regarding a doxepin food effect and/or that the doxepin should be administered with food, or at least in relatively close proximity to eating food or eating a meal (for example, within one hour or less). By way of example, such information or instructions could be provided orally or in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith.

It should be noted that some aspects of the invention also relate to methods of treating depression or anxiety by administering doxepin without food. Such embodiments can also include instructions to take the medication without food.

Improved Pharmacokinetic Consistency and Efficacy:

Still further embodiments relate to methods for improving the consistency of pharmacokinetics associated with doxepin therapy, in which a patient receives a multiple doxepin dosages over multiple days. The methods can include administering the doxepin to the patient in a fixed temporal relationship to food intake by the patient. Also, the method can further include providing instructions to the patient to take the doxepin in a fixed temporal relationship to food intake by the patient. As discussed more fully herein, taking doxepin in fixed or consistent temporal relationship to food can lead to improved safety and tolerability for the patient, for example, due to less variability in the drug kinetics in the patient.

Kits and Products:

Furthermore, some embodiments relate to kits and products for a therapy that includes the use of doxepin. The kits and products can include doxepin and instructions to take the doxepin without food or in a fasted state, or to take the doxepin with food or within a predetermined period of eating food.

The instructions or information regarding a food effect can be provided orally or verbally, or could be in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith or with information on where to access the instructions/information (e.g., a website).

Administration of Doxepin

In performing the methods, doxepin, a pharmaceutically acceptable salt of doxepin, or prodrug of doxepin can be administered in any suitable oral form. Also, doxepin, or a pharmaceutically acceptable salt or a prodrug thereof can be administered to a patient. (It should be understood that the term "administer" and its variants are intended to cover both self-administration and administration by another person or by a device).

Doxepin can be administered without food or in a fasted state. For example, doxepin can be administered at least about 30 minutes to about 4, 5, 6 or more hours after consuming food. More preferably, doxepin can be taken at least about 1 hour to about 6 hours after consuming food. In some aspects doxepin can be taken at least about 1, 2, 3, 4, 5 6 or more hours after consuming food.

Also, doxepin can be administered at least about 30 minutes to about 6 hours before consuming any food, or more preferably, at least about 1 hour to about 3 hours before consuming food. In some aspects, doxepin can be administered about 1, 2, 3 or more hours before food is consumed.

In some embodiments of the invention, such as when doxepin is used to facilitate sleep, instructions may be provided to patients receiving doxepin therapy or health care professionals involved in treatment of those patients that the doxepin should be administered without food, preferably separated from food for the time periods discussed above. Also, the patient can be provided with information regarding a doxepin food effect. In other embodiments of the invention, such as when doxepin is used to treat depression or anxiety, instructions may be provided to patients receiving doxepin therapy or health care professionals involved in treatment of those patients that the doxepin should be administered with food, or at least in relatively close proximity to eating food or eating a meal (for example, within one hour or less).

Again, by way of example, such instructions or information regarding a food effect could be provided orally or verbally, or could be in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith.

It should be recognized that in some cases, the food effect disclosed herein can appropriately play a part in designing customized dosing regimens that reflect the preferences of a particular healthcare professional or their patient. Thus, for example, in doxepin therapy (e.g., chronic doxepin therapy), such as therapy for depression or anxiety, it is customary to titrate the dosage; in other words, typically start with a lower dose and then increase it to the minimum dose that is sufficiently effective for the patient in question. In this type of situation, there may be instances when doxepin is administered without food, even though more drug will be required to achieve the same effect. In such cases, consistency is important to maintaining equivalent pharmacological effects. In other words, if a patient on chronic doxepin therapy is receiving a titrated dose that has been determined when the patient is consistently taking doxepin with food, or consistently taking doxepin without food, then food-induced variations in doxepin pharmacokinetics should not be a factor in therapeutic response or side effects. Thus, for chronic doxepin therapy, one embodiment includes administering doxepin in a consistent relationship to food intake, regardless of whether it is or is not taken with food.

Suitable routes of administration of doxepin can include any route in which significant quantities of drug reach the stomach, including oral, buccal, and sublingual administration.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Administration though oral pathways can be accomplished, for example, using a capsule, a tablet, a granule, a spray, a syrup, a liquid, powder, granules, pastes (e.g., for application to the tongue). Oral administration can be accomplished using fast-melt formulations, for example. For example, rapidly-melting strips or sheets that include the drug and suitable excipients can be prepared that dissolve quickly in the mouth, using well-known formulation technology. For buccal or sublingual administration, the compositions may take any suitable form, for example, tablets or lozenges. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores.

Pharmaceutical preparations which can be used orally include for example, liquid solutions, powders, and suspensions in bulk or unit dosage forms. Also, the oral formulations can include, for example, pills, tablets, granules, sprays, syrups, pastes, powders, boluses, pre-measured ampules or syringes, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

A variety of techniques for formulation and administration can be found in *Remington: The Science and Practice of Pharmacy* (20th ed, Lippincott Williams & Wilkens Publishers (2003)), which is incorporated herein by reference in its entirety.

Compositions

As mentioned above, doxepin, pharmaceutically acceptable salts, and/or prodrugs of the same can be used alone or in combination with other substances, such as for example, other insomnia or sleep medications, or with other medications that treat a primary illness. Doxepin alone or in combination with other drugs can be included as part of a composition. The compounds and compositions can include any suitable form of the compound for pharmaceutical delivery, as discussed in further detail herein.

The compositions and formulations disclosed herein also can include one or more pharmaceutically acceptable carrier materials or excipients. Such compositions can be prepared for storage and for subsequent administration. Acceptable carriers or diluents for therapeutic use are well known in the pharmaceutical art, and are described, for example, in the incorporated material of *Remington: The Science and Practice of Pharmacy* ($20^{th}$ ed, Lippincott Williams & Wilkens Publishers (2003)), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include sugars (such as lactose, sucrose, mannitol, sorbitol), starch powder, maize starch, wheat starch, rice starch, potato starch, gelatin, gum tragacanth, methyl cellulose, hydroxypropylmethyl-cellulose, sodium carboxymethylcellulose, or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone (PVP), and/or polyvinyl alcohol, saline, dextrose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. If desired, the compositions can include disintegrating agents may be added, such as the cross-linked polyvinyl pyrrolidone, agar, or alginic acid or a salt thereof such as sodium alginate. The pharmaceutical compositions can additionally include preservatives, solubilizers, stabilizers, wetting agents, emulsifiers, sweeteners, colorants, flavorings, buffers, coating agents, or antioxidants. Compositions for oral administration can be formulated according to conventional pharmaceutical practice as described in the incorporated material in *Remington: The Science and Practice of Pharmacy* ($20^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form.

One can also administer the compounds of the invention in sustained release forms or from sustained release drug delivery systems. A description of representative sustained release materials can be found in the incorporated materials in *Remington: The Science and Practice of Pharmacy* (20th ed, Lippincott Williams & Wilkens Publishers (2003)).

Dosage

The selected dosage level can depend upon, for example, the condition being treated, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. It will be understood, however, that the specific dose level for any particular patient can depend upon a variety of factors including the genetic makeup, body weight, general health, diet, time and route of administration, combination with other drugs and the particular condition being treated, and its severity. For the treatment of insomnia, preferably one dose is administered prior to bedtime.

As mentioned above, in some embodiments the preferable dosage can be between about 0.001 milligrams and about 350 milligrams. In some aspects, the dosage can be about 50 milligrams to about 350 milligrams. More preferably, the dosage can be between about 75 milligrams and 300 milligrams. Also, in some aspects, the dosage can be between about 0.1 milligrams and 20 milligrams or between about 0.5 milligrams and 10 milligrams. The dosage also can be between about 1 milligram and about 6 milligrams. Preferably, the dosage can be about 0.5 milligrams, 1 milligram, about 2 milligrams, about 3 milligrams, about 4 milligrams, about 5 milligrams or about 6 milligrams. Further, the dosage can be about 7 milligrams, about 8 milligrams, about 9 milligrams, or about 10 milligrams. The lower dosage ranges are particularly desirable for sleep-related indications, while the higher dosage ranges are particularly desirable for depression and anxiety-related indications.

EXAMPLES

Example 1

Assessment of the Effect of Food on the Pharmacokinetics of Doxepin

A study assessed the effect of food on the pharmacokinetics (PK) of doxepin in healthy subjects. It was a single-center, phase 1, randomized, open-label, single dose, two-way crossover study conducted in sixteen healthy, young adult male and female subjects. Screening procedures were performed within 14 days prior to enrollment.

Following screening procedures and baseline assessments, eligible subjects were randomly assigned to one of two treatment sequences (fed-fasted or fasted-fed). Subjects received a single 6 milligram dose of doxepin in the morning under either fed or fasted conditions on 2 dosing days (Day 1 and Day 8). There were approximately 7 days between each dose. Enrolled subjects were admitted to the study center on the evening before study drug dosing (Day 0 and Day 7) and remained at the study center for approximately 5 days. All subjects were dosed under both fed and fasted conditions during the study as illustrated in FIG. 1.

Subjects being dosed under fasted conditions were required to fast overnight for at least 10 hours prior to study drug administration and for 4 hours after study drug administration. Fluids were restricted from 1 hour predose to 1 hour postdose, except for water taken at the time of dosing. Subjects being dosed under fed conditions were dosed approximately 5 minutes after eating a high-fat, high-calorie standardized breakfast (to be ingested within 25 minutes). Subjects were required to ingest the entire contents of the breakfast. All subjects were required to remain in bed for approximately 4 hours after dosing.

Contents of the high-fat, high-calorie standardized breakfast were:
Two eggs fried in butter;
Two slices of bacon;
240 mL (8 fl. oz) whole milk;
57 g (2 oz) of hash browned potatoes; and
Two slices of toasted white bread with butter.

The total amount of protein, fat, and carbohydrate that made up this meal was approximately 33, 55, and 58 g, respectively. The total calorie content was approximately 850 kcal.

Subjects were dosed on Day 1 and Day 8. The PK profiles were evaluated on Days 1 through 5 and Days 8 through 12. Blood samples were collected at predose (0 hour) and at 0.08, 0.17, 0.25, 0.5, 0.75, 1, 1.5, 2, 3, 4, 6, 8, 12, 24, 36, 48, 60, 72, and 96 hours postdose. The samples were analyzed for doxepin and doxepin metabolite concentrations in plasma. Plasma concentrations of doxepin were measured using validated high performance liquid chromatography coupled to tandem mass spectrometry. The lower limit of quantification for doxepin was 0.05 ng/mL. The following PK parameters were estimated by noncompartmental methods using actual elapsed time from dosing:

| | |
|---|---|
| $C_{max}$ (ng/mL) | Maximum observed plasma concentration, obtained directly from the observed concentration versus time data. |
| $T_{max}$ (h) | Time to maximum plasma concentration, obtained directly from the observed concentration versus time data. |
| $AUC_{0-\infty}$ (ng · h/mL) | Area under the curve from time zero extrapolated to infinity, calculated by linear up/log down trapezoidal summation and extrapolated to infinity by addition of the last quantifiable concentration divided by the elimination rate constant ($AUC_{0-Tlast} + C_{last}/\lambda_z$). If the extrapolated area ($C_{last}/\lambda_z$) was greater than 30% of $AUC_{0-\infty}$, then $AUC_{0-\infty}$ was set to missing. |
| $AUC_{0-Tlast}$ (ng · h/mL) | Area under the curve from time zero to time of last measurable concentration, calculated by linear up/log down trapezoidal summation. |
| $AUC_{0-24}$ (ng · h/mL) | Area under the curve from time zero until 24 hours, calculated by linear up/log down trapezoidal summation. If the 24 h sample was missing or below the lower limit of quantification, $AUC_{0-Tlast}$ was to be reported as $AUC_{0-24}$. |
| $AUC_{0-48}$ (ng · h/mL) | Area under the curve from time zero until 48 hours, calculated by linear up/log down trapezoidal summation. If the 48 h sample was missing or below the lower limit of quantification, $AUC_{0-Tlast}$ was to be reported as $AUC_{0-48}$. |
| $AUC_{0-72}$ (ng · h/mL) | Area under the curve from time zero until 72 hours, calculated by linear up/log down trapezoidal summation. If the 72 h sample was missing or below the lower limit of quantification, $AUC_{0-Tlast}$ was to be reported as $AUC_{0-72}$. |
| $AUC_{0-96}$ (ng · h/mL) | Area under the curve from time zero until 96 hours, calculated by linear up/log down trapezoidal summation. If the 96 h sample was missing or below the lower limit of quantification, $AUC_{0-Tlast}$ was to be reported as $AUC_{0-96}$. |
| $\lambda_z$ (1/h) | Elimination rate constant associated with the terminal (log-linear) portion of the curve. This was estimated via linear regression of time versus log concentration. Visual assessment was used to identify the terminal linear phase of the concentration-time profile. A minimum of three data points were used for determination. |
| $t_{1/2}$ (h) | Apparent terminal half-life, determined as $\ln2/\lambda_z$. |
| CL/F (L/h) | Apparent oral clearance, calculated as dose divided by $AUC_{0-\infty}$. |
| Vd/F (L) | Apparent volume of distribution, calculated as $(CL/F)/\lambda_z$. |

Concentration-Time Profiles

With reference to Table 1, following a single 6 milligram dose administration of doxepin in fasted state (Treatment A) and fed state (Treatment B), mean plasma concentrations of doxepin increased, reaching $C_{max}$ at 3.0 and 6.0 hours postdose, respectively. Doxepin plasma concentrations, reached mean $C_{max}$ values of 0.854 and 0.951 ng/mL in fasted and fed states, respectively. For both treatments, plasma doxepin concentrations declined thereafter and remained quantifiable up to 48 hours postdose (the lower limit of quantification was 0.05 ng/mL). Detectable plasma levels of doxepin were first observed at 30 minutes postdose in both the fed and fasted states (six and five subjects, respectively). All subjects had detectable concentrations of doxepin by 90 minutes postdose. Median $T_{max}$ was delayed by approximately 3.0 hours in the fed state (6.0 hours) as compared to the fasted state (3.0 hours). However, the range of values was similar for both treatments. Mean $t_{1/2}$ values were comparable for fed and fasted states (16.5 versus 14.4 hours, respectively).

TABLE 1

Summary Statistics [arithmetic mean (CV %)] of Plasma Doxepin Pharmacokinetic Parameters

| | Treatment [a] | |
|---|---|---|
| Parameter (unit) | Fed (N = 16) | Fasted (N = 15) |
| $C_{max}$ (ng/mL) | 0.951 (58.8) | 0.854 (63.2) |
| $T_{max}$ (h)[b] | 6.0 (2.0-6.0) | 3.0 (1.5-6.0) |
| $AUC_{0-\infty}$ (ng · h/mL) | 18.6 (70.2) | 14.1 (80.6) |
| $AUC_{0-Tlast}$ (ng · h/mL) | 16.8 (74.0) | 12.6 (85.7) |
| $t_{1/2}$ (h) | 16.5 (23.8) | 14.4 (42.2) |
| $\lambda_z$ (1/h) | 0.0445 (26.6) | 0.0623 (65.9) |

[a] 6 milligram doxepin tablet, under fed or fasted conditions.
[b] Indicates median (range) values.

Table 2 shows the estimates of clearance and volume of distribution for doxepin. Mean CL/F and Vd/F were 43% and 14% lower in the fed state compared to the fasted state, respectively. Mean CL/F values were lower in the fed (477 L/h) versus the fasted (837 L/h) states. Mean Vd/F remained almost unchanged for fed (10280 L) and fasted (11930 L) states.

TABLE 2

Summary Statistics [arithmetic mean (CV %)] of Mean Clearance and Volume of Distribution for Doxepin

| | Treatment [a] | |
|---|---|---|
| Parameter (unit) | Fed (N = 16) | Fasted (N = 15) |
| CL/F (L/h) | 477 (63.4) | 837 (114.3) |
| Vd/F (L) | 10280 (43.3) | 11930 (46.9) |

[a] 6 milligram doxepin tablet, under fed or fasted conditions.

The effect of a high-fat meal on the pharmacokinetics of the 6 milligram doxepin tablet was assessed and statistical comparisons of doxepin pharmacokinetic parameters between treatments are presented in Table 3.

The 90% confidence intervals for the ratio of population geometric least-square means between fed and fasted treatments was not completely contained within the equivalence limits of 80-125% for $C_{max}$, and were outside the equivalence limits for $AUC_{0-\infty}$ and $AUC_{0-Tlast}$, indicating that there was a food effect on exposure. Under fed conditions, $AUC_{0-\infty}$, $AUC_{0-Tlast}$, and $C_{max}$ were higher by 41%, 46%, and 15%, respectively, compared to fasted conditions.

TABLE 3

Statistical Comparison of Doxepin Pharmacokinetic Parameters Between Treatments

| Parameter (unit) | Treatment [a] | N | Geometric LS Mean | Pairwise Comparisons Pair | Ratio (%) | 90% CI |
|---|---|---|---|---|---|---|
| $AUC_{0-\infty}$ (ng · h/mL) | Fed | 16 | 15.14 | Fed/ | 141.3 | (124.7, 160.1) |
|  | Fasted | 15 | 10.72 | Fasted |  |  |
| $AUC_{0-Tlast}$ (ng · h/mL) | Fed | 16 | 13.39 | Fed/ | 145.6 | (127.0, 166.9) |
|  | Fasted | 15 | 9.194 | Fasted |  |  |
| $C_{max}$ (ng/mL) | Fed | 16 | 0.822 | Fed/ | 114.6 | (101.8, 129.1) |
|  | Fasted | 15 | 0.717 | Fasted |  |  |

Note:
Results are based on mixed effect analysis of variance with sequence, period and treatment as fixed effects and subject within sequence as a random effect.
[a] 6 milligram doxepin tablet, under fed or fasted conditions.

CONCLUSIONS

Following a single 6 milligram dose of doxepin, a food effect was observed on the pharmacokinetics of doxepin. In the fed state, the maximum concentration ($C_{max}$) and exposure ($AUC_{0-\infty}$) of doxepin were approximately 15% and 41% higher, respectively, compared to the fasted state, and median $T_{max}$ was delayed by approximately 3.0 hours. The increase in exposure was statistically significant and represents an increase in bioavailability in the fed state (Table 4).

TABLE 4

| Parameter | Arithmetic Mean (Fed condition) | Arithmetic Mean (Fasted condition) | Effect of Food (% of fasted state)[a] |
|---|---|---|---|
| $AUC_{0-\infty}$ (ng · h/mL) | 18.6 | 14.1 | 141 |
| $C_{max}$ (ng/mL) | 0.951 | 0.854 | 115 |
| $T_{max}$ (h)[b] | 6 | 3 | 200 |

[a] Note that percentages documenting food effect on $C_{max}$ and AUC are calculated from geometric LS means rather than the arithmetic means presented in this table
[b] $T_{max}$ is presented as a median value Many modifications and variations of the embodiments described herein may be made without departing from the scope, as is apparent to those skilled in the art. The specific embodiments described herein are offered by way of example only.

We claim:

1. A method for providing sleep therapy comprising administering a 3 mg or a 6 mg dose of doxepin to an individual at least three hours after consuming a meal, thereby providing a faster onset of action and reducing next day residual effects.

2. The method of claim 1, wherein the administration comprises self administration by the individual.

3. The method of claim 1, wherein the doxepin is administered in a dose of 3 mg.

4. The method of claim 1, wherein the doxepin is administered in a dose of 6 mg.

5. The method of claim 1, wherein the doxepin is administered as a tablet, capsule or liquid.

6. The method of claim 5, wherein the doxepin is administered as a tablet.

7. The method of claim 1, wherein the doxepin is administered as a unit dosage form.

8. The method of claim 1, wherein the doxepin is administered as an oral dosage form.

9. A method of minimizing next day residual sedation caused by doxepin sleep therapy, comprising providing doses of 3 mg or 6 mg of doxepin to a patient and instructing the patient not to take the doxepin within three hours of consuming a meal.

10. The method of claim 9, comprising providing the patient with a 6 mg dose of doxepin.

11. The method of claim 9, comprising providing the patient with a 3 mg dose of doxepin.

12. The method of claim 9, wherein the doxepin is provided as a tablet, capsule or liquid.

13. The method of claim 12, wherein the doxepin is provided as a tablet.

14. The method of claim 9, wherein the doxepin is provided as a unit dosage form.

15. The method of claim 9, wherein the doxepin is provided as an oral dosage form.

16. In a method of treating insomnia with doxepin, wherein an insomnia patient receives a dosage of between 0.5 and 7 mg of doxepin, the improvement comprising altering the pharmacokinetics of doxepin by providing the patient with doxepin and providing instructions to take the doxepin at least three hours after a meal, such that upon taking the doxepin per said instructions, the pharmacokinetics are altered by decreasing the time to reach maximum plasma concentration ($T_{max}$) in the patient, reducing the maximum plasma concentration ($C_{max}$), and reducing the area under the curve (AUC) compared to administering the doxepin with food.

17. The method of claim 16, wherein the doxepin is provided in an amount of about 3 mg.

18. The method of claim 16, wherein the doxepin is provided in an amount of about 6 mg.

19. The method of claim 16, wherein the instructions further instruct the patient to take a dosage of 6 mg.

20. The method of claim 16, wherein the instructions further instruct the patient to take a dosage of 3 mg.

21. The method of claim 16, wherein the doxepin is provided as a tablet, capsule or liquid.

22. The method of claim 21, wherein the doxepin is provided as a tablet.

23. The method of claim 16, wherein the doxepin is provided as a unit dosage form.

24. The method of claim 16, wherein the doxepin is provided as an oral dosage form.

* * * * *